US012558537B2

(12) United States Patent
Makharinsky et al.

(10) Patent No.: US 12,558,537 B2
(45) Date of Patent: Feb. 24, 2026

(54) DELIVERY SYSTEMS AND METHODS FOR POSITION PRE-CHECK AND ATRAUMATIC IMPLANTATION OF A CARDIAC PACING LEAD

(71) Applicant: Eagle Point Medical LLC, City Of Dover, DE (US)

(72) Inventors: Leonid Makharinsky, Bonassola (IT); Brian Houston Craig, Minneapolis, MN (US)

( * ) Notice: Subject to any disclaimer, the term of this patent is extended or adjusted under 35 U.S.C. 154(b) by 278 days.

(21) Appl. No.: 18/401,672

(22) Filed: Jan. 1, 2024

(65) Prior Publication Data

US 2024/0382747 A1 Nov. 21, 2024

Related U.S. Application Data

(60) Provisional application No. 63/471,479, filed on Jun. 6, 2023, provisional application No. 63/467,058, filed on May 17, 2023.

(51) Int. Cl.
*A61N 1/05* (2006.01)
*A61M 25/00* (2006.01)
*A61N 1/37* (2006.01)

(52) U.S. Cl.
CPC ....... *A61N 1/0565* (2013.01); *A61M 25/0043* (2013.01); *A61N 1/056* (2013.01); *A61N 1/3702* (2013.01); *A61N 1/371* (2013.01); *A61M 2025/0063* (2013.01)

(58) Field of Classification Search
None
See application file for complete search history.

(56) References Cited

U.S. PATENT DOCUMENTS

| | | |
|---|---|---|
| 11,045,653 B1 | 6/2021 | Makharinsky et al. |
| 2002/0077583 A1 | 6/2002 | Clemens et al. |
| 2004/0082986 A1 | 4/2004 | Westlund et al. |
| 2004/0116878 A1* | 6/2004 | Byrd ...................... A61N 1/056 607/116 |
| 2014/0288576 A1 | 9/2014 | Bornzin et al. |

OTHER PUBLICATIONS

Vijayaraman P, Subzposh FA, Naperkowski A, et al. Prospective evaluation of feasibility and electrophysiologic and echocardiographic characteristics of left bundle branch area pacing. Heart Rhythm 16:1774-1782, 2019.

* cited by examiner

*Primary Examiner* — Carl H Layno
*Assistant Examiner* — Bryan McAllister Lee
(74) *Attorney, Agent, or Firm* — Boris Leschinsky

(57) ABSTRACT

A novel delivery system for implantation of a cardiac pacing lead comprising an elongated delivery sheath sized to accept the cardiac pacing lead inside thereof and an electrically-active elongated stylet positioned along the cardiac pacing lead and having a first distal electrode configured to provide a first electrical connection to the proximal end of the elongated stylet. The implantation method includes a step of pre-checking a first position in the cardiac tissue by temporarily confirming the ability to deliver the pacing therapy at that position using the first distal electrode of the elongated stylet. If the first position is determined to be acceptable, the cardiac pacing lead is implanted at that position. Otherwise, the delivery system is moved to another position without any significant trauma to the cardiac tissue at the first position.

18 Claims, 13 Drawing Sheets

10

23

25

21

16

32

27

18

30

31

22

18

30

31

30

31

DELIVERY SYSTEMS AND METHODS FOR POSITION PRE-CHECK AND ATRAUMATIC IMPLANTATION OF A CARDIAC PACING LEAD

CROSS-REFERENCE DATA

This application claims a priority date benefit from the U.S. Provisional Patent Application No. 63/471,479 filed 6 Jun. 2023 by the same inventor and entitled "SYSTEMS AND METHODS FOR POSITION PRE-CHECK AND ATRAUMATIC CARDIAC PACING LEAD IMPLANTATION," incorporated herein by reference in its entirety.

This application further claims a priority date benefit from the U.S. Provisional Patent Application No. 63/467,058 filed 17 May 2023 by the same inventor and entitled "LEFT BUNDLE BRANCH PACING CATHETER WITH DEPTH CONTROL USING A MULTI-ELECTRODE LEAD WITH A FIXED OR AN EXTENDABLE-RETRACTABLE TIP," also incorporated herein by reference in its entirety.

BACKGROUND

Without limiting the scope of the invention, its background is described in connection with cardiac pacing leads. More particularly, the invention describes a lead delivery system configured to identify and verify the most suitable lead implantation position prior to actually deploying the lead into the cardiac tissue.

Hundreds of thousands of cardiac pacing leads are implanted in the United States each year. Cardiac pacing is a common procedure used to treat various cardiac conditions, including bradycardia and heart block. Although the present disclosure is primarily focused on the implantation of the pacing lead into the interventricular septum to provide conduction system pacing for a wide variety of bradycardia indications or cardiac resynchronization therapy for patients with bundle branch block and cardiac dyssynchrony/cardiomyopathy, it is assumed that similar procedures and methods may be used for cardiac lead implantation in other areas of the heart. The concepts described herein may also be adapted for lead implantation in other areas of the body, such as in the brain, spine, or other locations, as the invention is not limited in this regard.

Conduction system pacing is a promising new treatment that is anticipated to replace the traditional right ventricular apical pacing for the vast majority of standard pacing indications. Additionally, the same technique can be used instead of traditional bi-ventricular pacing for cardiac resynchronization therapy.

About 300,000 pacemakers are implanted every year in the US. According to the American Heart Association, around 30% to 40% of patients who undergo pacemaker implantation have a so-called left bundle branch block, or LBBB.

Percutaneous lead implantation for cardiac pacing purposes, including specifically targeting the interventricular septum to treat the above-mentioned subgroups of patients and provide conduction system pacing, involves several steps:

a. Patient Preparation: The patient is prepared by disinfecting the site of lead insertion, typically in the left upper chest region. Local anesthesia is administered to numb the area, ensuring the patient's comfort during the procedure;

b. Access and Guidewire Placement: A small incision is made, and a sheath is inserted into a vein, usually the subclavian vein. Using fluoroscopic guidance, a guidewire is advanced through the sheath and directed towards the heart, specifically the right atrium, followed by a delivery sheath in some cases;

c. Lead Advancement: A cardiac lead, which consists of an insulated wire with at least one electrode at the tip, is threaded inside the sheath and carefully advanced into the right atrium. Fluoroscopy is used to visualize the lead's progress and ensure it is correctly positioned;

d. Interventricular Septum Deployment: Once the delivery system comprising a guiding sheath with a special shape reaches the right atrium, it is directed through the tricuspid valve and toward the interventricular septum. The lead's tip is then advanced slightly out of the sheath and positioned in a suitable location guided by a variety of criteria. It is then advanced by rotation, applying pressure to the septum to reach a suitable depth within the septum to enable optimal pacing and capture of the conduction system;

e. Confirmation and Testing: Once the lead is in position, its placement is confirmed using fluoroscopy, contrast injection (in some cases) and electrical measurements. The pacing thresholds and sensing abilities of the lead are assessed to ensure proper functionality and accurate detection of cardiac signals;

f. Lead Fixation and Closure: After confirming the lead's satisfactory placement, the delivery sheath is removed, and the lead is secured in place. The incision site is then closed using standard methods;

g. Post-Procedure Monitoring: Following the implantation, the patient is monitored to ensure there are no complications such as bleeding, infection, or pneumothorax. Chest X-rays may be performed to verify lead position and check for any associated lung complications.

A percutaneous lead implantation into the interventricular septum for conduction system pacing is a meticulous procedure that requires skill and expertise. The goal is to position the lead accurately within the septum of the heart to provide effective pacing, conduction system capture, and restore normal electrical conduction. In particular, a selection of a proper location in the septum near the conduction system (typically, the left bundle branch and its tributaries) and advancing the electrode tip to a suitable depth is a somewhat uncertain step of the procedure. It is not uncommon to deploy the lead tip into a septum only to find out that the conduction system capture cannot be properly obtained. The lead, in this case, may be pulled back by rotation and implanted at another adjacent location. In some cases, several deployments of the lead in various positions in the septum are still not resulting in the desired pacing capability, and the lead implantation procedure has to be abandoned in favor of alternative treatment, such as, for example, traditional ventricular pacing or bi-ventricular pacing. Multiple deployments of a larger lead tip into the septum create unnecessary septal damage and extend procedure time, and, therefore, should be avoided if at all possible.

The need exists, therefore, for a less traumatic method and system for lead deployment, which allows for more rapid identification of a proper pacing location and implantation depth, which avoids the limitations of the current procedure.

SUMMARY

Accordingly, it is an object of the present invention to overcome these and other drawbacks of the prior art by providing a novel delivery system and a deployment method aimed at minimizing the trauma to the cardiac tissue associated with multiple delivery attempts at properly positioning a pacing lead.

It is another object of the present invention to provide a novel delivery system and an implantation method that minimizes the time required to find a reliable implantation position for the pacing lead.

It is a further object of the present invention to provide a novel delivery system and implantation method for implanting a cardiac pacing lead after the implantation site is pre-checked to assure its suitability for delivering the intended cardiac pacing therapy.

The delivery system for implantation of a cardiac pacing lead may include an elongated delivery sheath sized to accept the cardiac pacing lead inside thereof. It may be made to be slightly larger than a conventional pacing lead delivery sheath to contain an elongated stylet positioned along with and in parallel with the cardiac pacing lead. In some embodiments, both the elongated stylet and the pacing lead are placed next to each other in the same lumen of the elongated delivery sheath. In other embodiments, the elongated delivery sheath has a dedicated lumen for the pacing lead and a separate dedicated lumen for the elongated stylet.

The elongated stylet has a distal end and a proximal end. The distal end of the elongated stylet may feature a first distal electrode configured to provide a first electrical connection to the proximal end of the elongated stylet, such as by using alligator clips or other conventional electrical connections. The delivery sheath may be configured to allow the cardiac pacing lead and the stylet to be advanced inside the delivery sheath independently of one another.

In other embodiments, the elongated stylet may include a second or more electrodes at the distal end of the elongated stylet, with each distal end electrode configured for independent operation of providing electrical stimulation to the heart and/or for recording an electrogram of the heart's electrical activity at the location of the distal end of the elongated stylet.

A novel method for delivery of a cardiac pacing lead selected to provide prescribed pacing therapy to a target cardiac tissue may include the steps of:

a. providing a delivery system comprising an elongated delivery sheath containing the cardiac pacing lead and an elongated stylet inside thereof, b. positioning a distal end of the delivery sheath adjacent to a target cardiac tissue, c. advancing the elongated stylet to a first position for implantation of the cardiac pacing lead, such as a position deep into the interventricular septum—while continuously or intermittently monitoring cardiac pacing parameters, d. pre-check the first position in the cardiac tissue by temporarily confirming the ability to deliver the pacing therapy thereat, such as according to a predetermined acceptance criterion, e. if the confirmation is not reached in step (d), changing the depth of the distal end of the elongated stylet or repositioning the delivery system and the elongated stylet to a second position or further positions and repeating the step of temporarily confirming the ability to deliver the pacing therapy thereat, f. upon reaching the confirmation in step (d) or step (e), deploying the cardiac pacing lead to the position next to the distal end of the elongated stylet, and g. withdrawing the elongated stylet and removing the delivery system while leaving the cardiac pacing lead in the target cardiac tissue.

If no confirmation of therapy delivery is achieved at any of the depths in the first position of the delivery sheath, the sheath may be repositioned to another nearby location and the implantation procedure may be repeated until a proper location and depth are identified.

The system and method of the invention allow finding the most appropriate position for lead implantation faster and with less trauma to the cardiac tissue as compared to traditional lead implantation techniques.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through the use of the accompanying drawings, in which:

DETAILED DESCRIPTION OF PREFERRED EMBODIMENTS OF THE INVENTION

Figures 1, 2, 3:
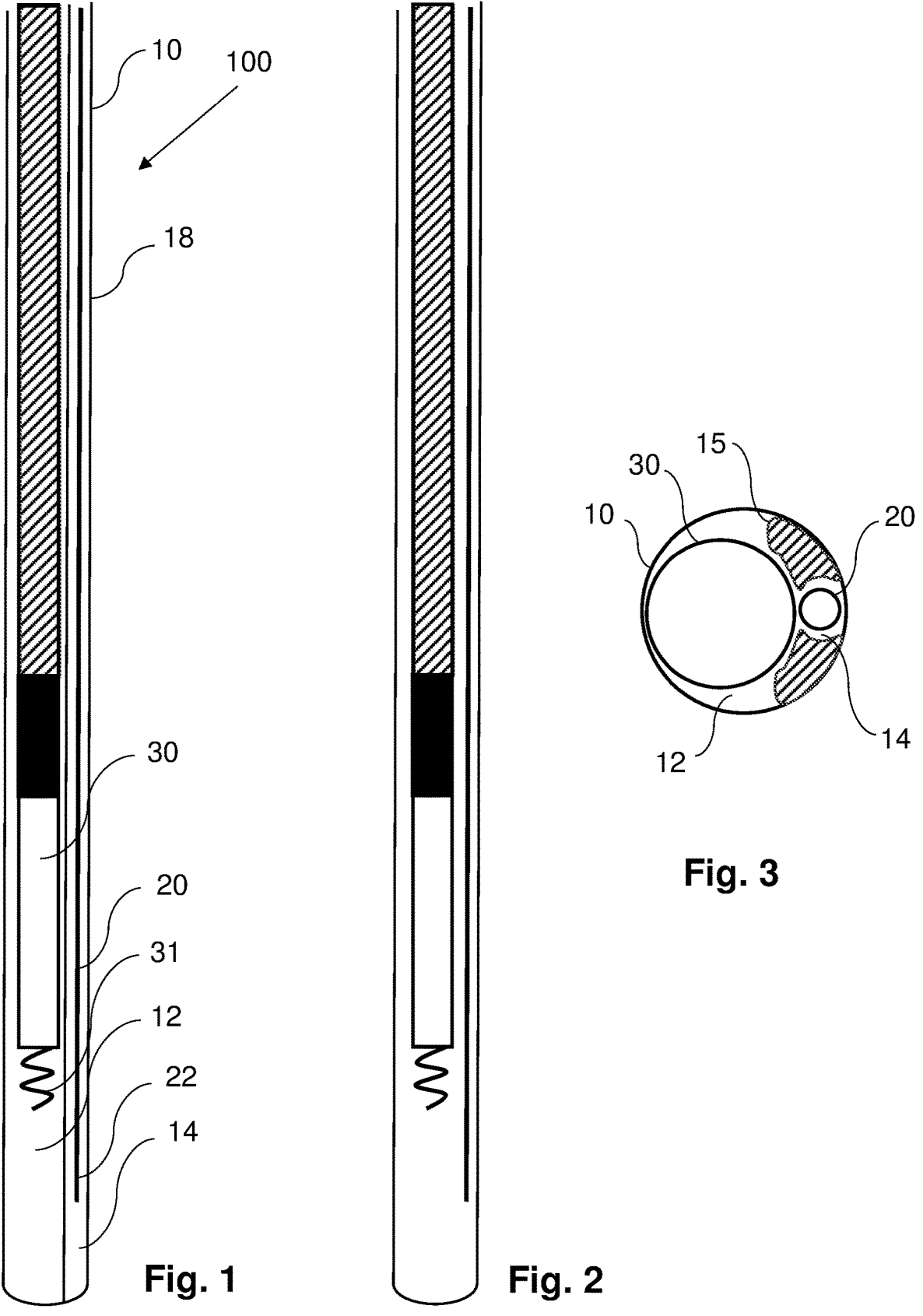
FIG. 1 is a schematic longitudinal cross-sectional view of the distal end of the delivery sheath with two lumens for the pacing lead and the elongated stylet.
FIG. 2 is a schematic longitudinal cross-sectional view of the distal end of the alternative design for the delivery sheath with a common lumen for the pacing lead and the elongated stylet.
FIG. 3 is a cross-sectional view of yet another design of the delivery sheath with both lumens shown as partially joined.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Various methods and systems to determine the preferred implantation location using novel pacing leads are described by the inventors of the present invention in previously filed patent applications. One such document is the international patent application No. PCT/US21/036440 filed 8 Jun. 2021, incorporated herein by reference.

The present disclosure is concerned with providing systems and methods aimed at assisting in the delivery and implantation of a conventional cardiac pacing lead, which may be provided without modifications thereof or with small changes that do not affect its primary function in a major manner. One example of a suitable pacing lead used for conduction system pacing and generally configured for implantation into the interventricular septum is the Select-Secure cardiac pacing lead Model 3830 by Medtronic. Other pacing leads on the market have larger outer diameters and larger helical tips that can induce even more damage to the cardiac tissue if repositioned several times. Other manufacturers also produce suitable leads for the same purpose or a different purpose, as the invention is not limited in this regard. One advantage of the present invention is that it may be used to deliver such conventional pacing lead but with a new advantage of pre-checking the implantation location before committing to inserting the distal end of the pacing lead into the cardiac tissue.

The main advantage of the present invention is to avoid multiple tissue penetrations by the pacing lead, which typically create multiple "channels" in the septum by a comparatively large tip of a cardiac pacing lead equipped with a helix. The invention allows a clinician to pre-check the target location with less invasive means before proceeding with the actual implantation of the pacing lead itself. In other words, the invention describes methods and systems configured to probe one or more cardiac tissue locations at various depths, such as at the interventricular septum to determine the best location and an appropriate depth of implantation prior to advancing and deploying the cardiac lead into the heart tissue.

FIG. 1 shows a general diagram of the distal end of the cardiac pacing lead delivery system 100 according to the present invention. A conventional cardiac lead 30 may be located along with an elongated stylet 20 throughout the entire length or at least within a distal portion 18 of the elongated delivery sheath 10. FIG. 1 shows the sheath 10 as having two lumens: a first lead lumen 12 configured to house the pacing lead 30 and a separate second stylet lumen 14 configured to house the elongated stylet 20. In other embodiments, both the lead 30 and the stylet 20 may reside in a single lumen of the sheath 10, as seen in FIG. 2, provided that the lumen is large enough to accommodate both the lead 30 and the elongated stylet 20 positioned side by side and allows for either one of these components to freely slide past the other, in further embodiments, the first lumen 12 and the second lumen 14 may be partially joined so as to reduce the overall diameter of the delivery sheath, and yet provide for separation of the pacing lead 30 from the elongated stylet 20 as one slides past the other. One example of such arrangement is a cross-section seen in FIG. 3 with one or two partial dividers 15 to keep the pacing lead 30 and the elongated stylet 20 separated from each other in their respective first lumen 12 and second lumen 14.

The distal portion 18 of the delivery sheath 10 may also have other features similar to other lead delivery systems, such as one or more external electrodes at the distal end thereof, or one or more radiopaque markers, as the invention is not limited in this regard (not shown in the drawings). In further embodiments, the distal end 18 may have one or more preshaped configurations to better facilitate delivery of the stylet 20 and the pacing lead 30 to the desired location. In further yet embodiments, the distal end 18 may be malleable or deflectable as known in the art.

Figures 4, 5:
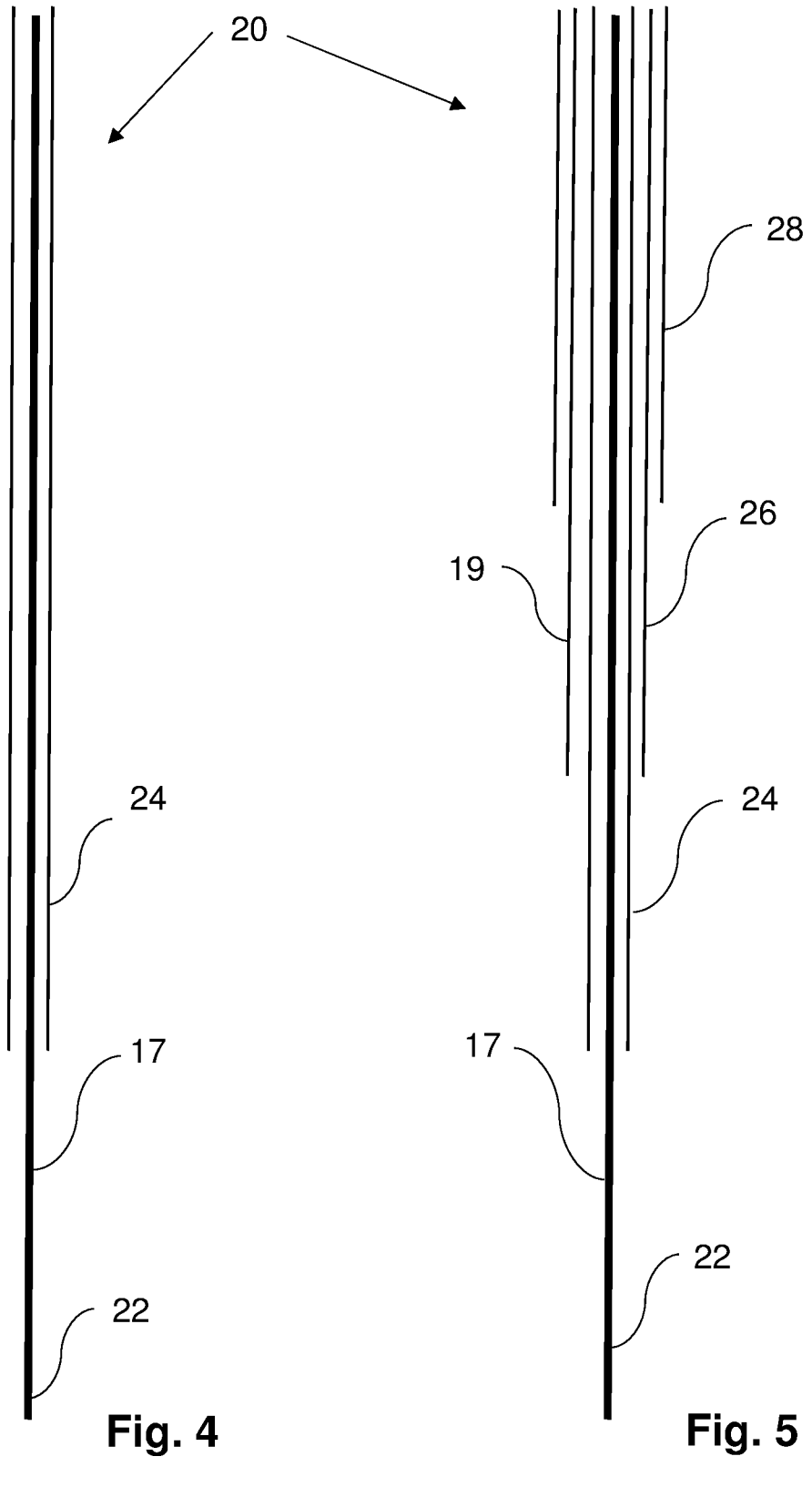
FIG. 4 is a longitudinal cross-sectional view of the distal end of the first embodiment of the elongated stylet.
FIG. 5 is a longitudinal cross-sectional view of the distal end of the second embodiment of the elongated stylet.
Figures 6, 7:
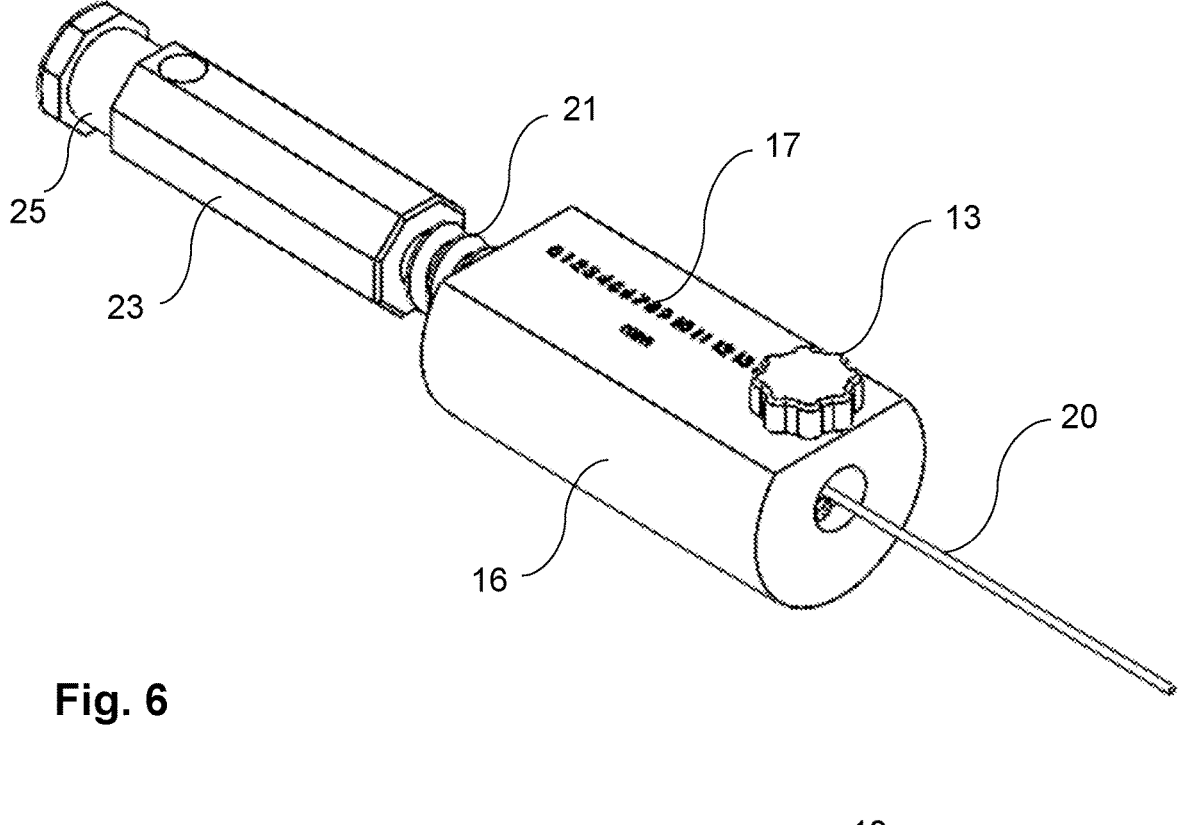
FIG. 6 is a perspective side view of the proximal portion of the elongated stylet within the retaining hub.
FIG. 7 is a cross-sectional side view of the proximal end of the elongated stylet within the retaining hub.

The elongated stylet 20 of the invention may have a first electrode 17 in the form of a single exposed conductor 22 at the distal end thereof, as seen in a closeup diagram in FIG. 4. The rest of the body of the stylet may be covered with an isolating coating (such as a PTFE or another suitable coating) or a thin polymer sheath 24 (such as a shrink wrap). The proximal end of the elongated stylet 20 may be configured to be electrically connected to a cardiac stimulator and monitor (not shown in the drawings) through a snap-on first rapid connection area 25, as seen in FIG. 6. The elongated stylet 20 may be made from stainless steel, Nitinol, or another suitable metal or metal alloy. The distal end 22 may be made straight or contain a fixation spiral tip (not shown) configured to temporarily deploy and retain the stylet 20 in the cardiac tissue. It may also contain a small sphere at the end to minimize the risk of unintended tissue trauma and avoid damaging or piercing while inside the delivery system.

In further embodiments, the initial shape of the elongated stylet 20 may be pre-formed to have a desired profile to improve the delivery position for the pacing lead 30, as the invention is not limited in this regard. Non-limiting examples of suitable pre-formed stylet profiles include those that are known to be used for a distal end of the delivery sheath, as may be appreciated by those skilled in the art. In other embodiments, the distal end of the elongated stylet may contain a curve such that rotating the elongated stylet with the curved distal end extended from the delivery sheath allows contact with a different location of the cardiac tissue.

In at least some embodiments, the elongated stylet may have markings on the proximal end that provide information about how far the proximal end of the elongated stylet is protruding beyond the distal end of the delivery sheath, providing guidance on the depth of the elongated stylet deployed in cardiac tissue.

The elongated stylet may have a length greater than that of the delivery sheath so as to allow the distal end of the elongated stylet protruding from the distal end of the delivery sheath while still having manual control of the proximal end of the elongated stylet protruding from the proximal end of the delivery sheath.

In further yet embodiments, the elongated stylet 20 may have a second electrode 19 or even more distal electrodes, as schematically illustrated in FIG. 5. These additional electrodes may terminate at the proximal end of the elongated stylet 20 with corresponding rapid connection areas, together forming the connection area 25. In this case, the initial electrically conductive material of the elongated stylet 20 may be first coated with an electrically isolating coating 24, exposing a first electrode 17 in the shape of the conductive distal end 22. A second electrically conductive coating 26 may be applied over the non-conductive coating 24 at a predefined distance further away from the distal end 22. Subsequently, a third non-conductive coating 28 may be applied to the external surface of the stylet 20 with a further step back from the end of the conductive coating 26, thereby forming a second distal end electrode 19 in the area where the second conductive coating 24 has an exposed outer surface to be in contact with blood or cardiac tissue. A similar arrangement may be applied to the connection area 25 (see FIG. 6) at the proximal end of the elongated stylet 20 so as to create suitable contact zones for activating the first distal end electrode 17 as well as additional distal electrodes 19, as described in greater detail below.

Figure 8:
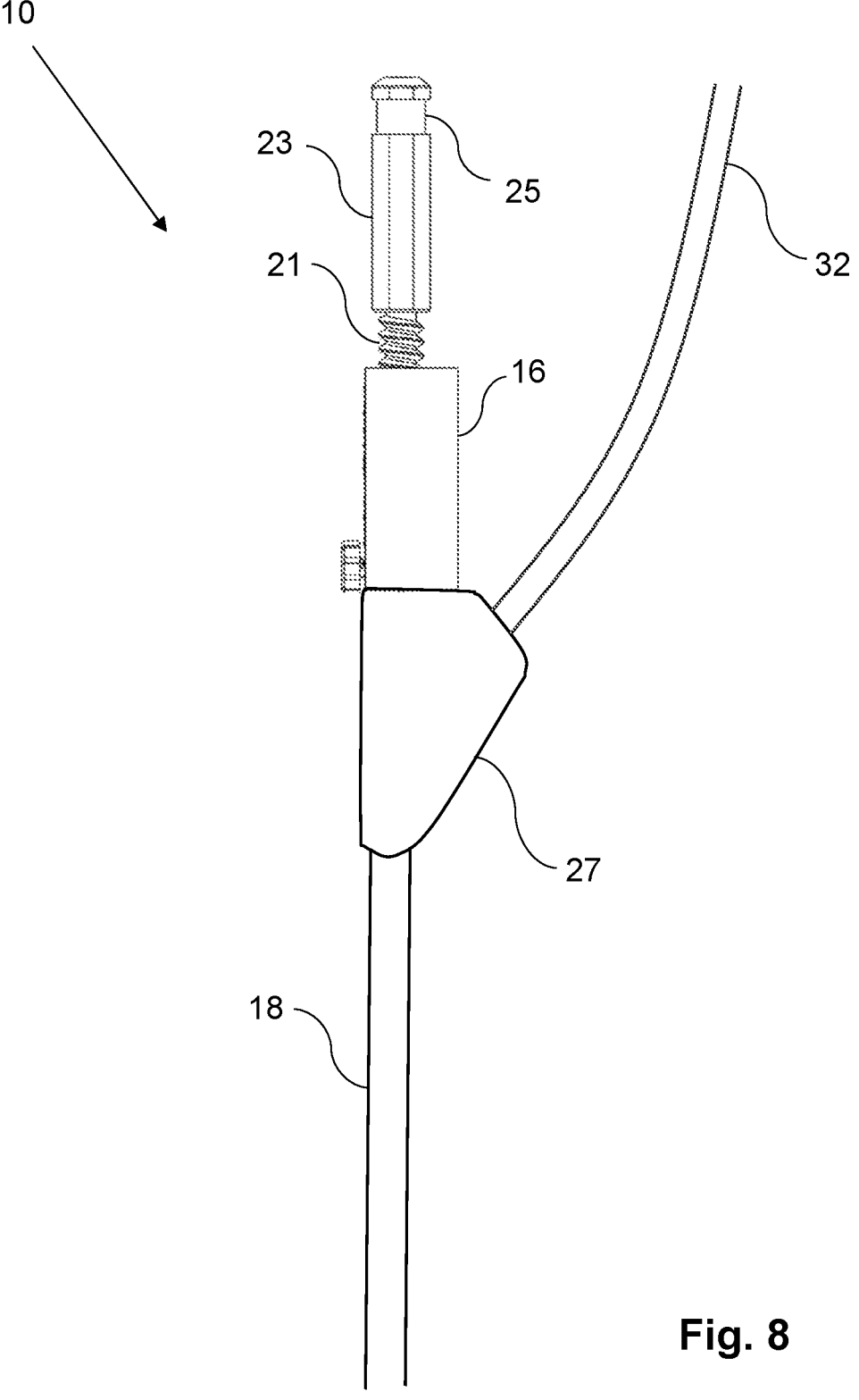
FIG. 8 is a side view of the proximal end of the delivery system of the present invention.

A perspective view in FIG. 6 and a side view in FIG. 7 show a general illustration of the proximal end of the elongated stylet within a retaining hub of the present invention. The delivery sheath 18 may be terminated with a Y-connector 27 with the retaining hub 16 removably or permanently attached to the portion thereof in straight alignment with the direction of the sheath 18. This arrangement may be advantageous to facilitate easy movement of the elongated stylet, which is generally straight in the proximal portion thereof through the retaining hub 16 and the Y-connector 27. The Y-connector 27 may have a second opening for the insertion of the cardiac lead 30, such as through an optional lumen 32, as seen in FIG. 8. In further embodiments, the Y-connector 27 may have further lumens, one-way valves, sealing diagrams, etc.—for example a side-arm for flushing the delivery sheath with saline, as the invention is not limited in this regard.

The retaining hub 16 may be configured to allow a controlled or a metered advancement of the elongated stylet 20 therethrough. One exemplary mechanism for a metered advancement of the elongated stylet 20 may comprise a threaded stylet portion 21 extending distally from the stylet handle 23, which cooperates with an internal threaded channel inside the retaining hub 16, which may be optionally made to be translucent or transparent. Making the retaining hub 16 transparent allows observing the position of the threaded stylet portion 21 inside the hub, which may also include position-indicating indicia 17. The engaged position of the distal edge of the threaded stylet portion 21 within the corresponding internal threaded channel of the hub 16 signifies the extent of protrusion of the stylet's distal end 22 located at the distal end of the delivery sheath 18. Rotating the stylet handle 23 causes a gradual advancement of the stylet's distal end 22 from the sheath and into the cardiac tissue, as explained in greater detail below. Not only this arrangement limits the depth of protrusion of the distal end 22 from the sheath 18, but the position-indicating indicia on the hub 16 may be used to assess the exact depth of stylet 20 deployment into the heart tissue. Once a desired protrusion of the elongated stylet is achieved, an optional fixation screw 13 may be used to retain the elongated stylet in place within the hub 16.

In further embodiments, other metered advancement mechanisms may be deployed instead of the threaded arrangement of components 21 and 16. One example of such a design is a sliding arrangement of one component inside the other, as the invention is not limited in this regard.

Furthermore, the deployment sheath 18 may be designed as a stand-alone component, with the retaining hub 16 incorporating the metered advancement mechanism as described above capable of attaching to and detaching therefrom. In other embodiments, a conventional delivery sheath 18 may be used, and the hub 16 with its internal threaded channel may be attached thereto to convert the conventional delivery sheath to perform the action of metered advancement of the stylet 20.

In further yet embodiments, a second metered advancement mechanism may also be included for the deployment of the lead 30 (not shown in the drawings), thereby providing for a more complete individual control of the advancement of each of the elongated stylet 20 and the pacing lead 30 into the depth of the target cardiac tissue.

Finally, external electrode attachment areas may be provided on or extended from the retaining hub 16 of the delivery sheath 10 to operate one or more distal electrodes on the body of the sheath 18, if present.

The cardiac lead 30 may be a conventional cardiac pacing lead configured for the purposes of providing cardiac pacing in the corresponding area of the heart, such as the interventricular septum. The pacing lead 30 may optionally include a stationary or a movable spiral tip at the distal end or other tissue fixation means. The pacing lead 30 may include one or more distal pacing electrodes or a defibrillator coil. In embodiments, the pacing lead 30 may be equipped with its own radiopaque markers (not shown). The pacing lead 30 may have a solid flexible core or include a central opening for advancing a dedicated lead stylet within thereof. In this case, the use of two electrically-active elongated stylets (one in the body of the pacing lead 30 and the other elongated stylet 20 adjacent to the lead 30) may be more advantageous.

FIGS. 9a through 9f illustrate specific exemplary steps of the deployment method of the cardiac pacing lead 30 into the cardiac tissue once the distal end of the delivery sheath 18 is positioned adjacent to the first likely position of lead implantation. Of note is that while the figures show the presence of all components together (the delivery sheath 18 contains both the pacing lead 30 and the elongated stylet 20), this may not be the case. In alternative embodiments, only the delivery sheath 18 may be deployed first, and the elongated stylet 20 may be delivered at a later phase of the procedure, followed by a separate delivery of the pacing lead 30. Having the elongated stylet 20 and/or the pacing lead 30 "preloaded" in the delivery sheath 18 is optional and may be decided based on the desired stiffness and other delivery considerations, as the invention is not limited in this regard.

In broad terms, the method for delivery of a cardiac pacing lead selected to provide a pacing therapy to a target cardiac tissue comprising the steps of:

a. providing a delivery system comprising an elongated delivery sheath containing the cardiac pacing lead and an elongated stylet inside thereof, b. positioning a distal end of the delivery sheath adjacent to a target cardiac tissue, c. advancing the elongated stylet to a first position for implantation of the cardiac pacing lead, d. pre-check the first position in the cardiac tissue by temporarily confirming the ability to deliver the pacing therapy thereat, e. if the confirmation is not reached in step (d), changing the depth of the distal end of the elongated stylet or repositioning the delivery system and the elongated stylet to a second position, such as a few millimeters away, or further positions and repeating the step of temporarily confirming the ability to deliver the pacing therapy thereat, f. upon reaching the confirmation in step (d) or step (e), deploying the cardiac pacing lead to the position next to the distal end of the elongated stylet, and g. withdrawing the elongated stylet and removing the delivery system while leaving the cardiac pacing lead in the target cardiac tissue.

In steps (d) or (e), the step of temporarily confirming the ability to deliver the pacing therapy using the elongated stylet may further include a step of pacing the heart using the distal end of the elongated stylet. As an alternative, or in addition, it may further include a step of monitoring an electrogram signal. Such signal may be acquired using the distal end of the elongated stylet or other electrodes configured to record the electrical activity of the heart.

The capturing of the conduction system of the heart may be confirmed using one or several criteria as accepted in the field of cardiac pacing. For example, Marek Jastrzębski et al. discuss various criteria for determining the capture of the conduction system, see Jastrzębski M et al. Left bundle branch area pacing outcomes: the multicentre European MELOS study, European Heart Journal (2022) 43, 4161-4173, incorporated herein it its entirety by reference. Other criteria may also be used, as the present invention is not limited in this regard—it provides the necessary tool to temporarily assess and therefore pre-check the position of the implantation of a cardiac pacing lead prior to the actual implantation thereof at that location.

Several other criteria may be considered to be indicative of left bundle branch area capture such as the following non-limiting examples:

a) appearance of a characteristic paced QRS complex on the 12-lead ECG, typically showing an incomplete right bundle branch block, when the lead reaches the final position near the left bundle branch, b) short peak left ventricular activation time as defined in a Vijayaraman's publication (Vijayaraman P, Subzposh F A, Naperkowski A, et al. Prospective evaluation of feasibility and electrophysiologic and echocardiographic characteristics of left bundle branch area pacing. Heart Rhythm 2019; 16:1774-1782.), typically less than 80 ms from the stimulus to the peak of the QRS in lead V6 in patients with narrow baseline QRS, c) two different paced QRS morphologies during threshold testing may be considered to be indicative of conduction system capture, d) a delay of more than 40 ms between the QRS peak in lead V6 and lead V1, e) characteristic changes in pacing impedance indicative of the electrode reaching a certain depth in the septum may also be used to access the lead progression into the septum (see Orlov M V, Nikolaychuk M, Koulouridis I, Goldman A, Natan S, Armstrong J, Bhattacharya A, Hicks A, King M, Wylie J. Left bundle area pacing: Guiding implant depth by ring measurements. Heart Rhythm. 2023 January; 20(1):55-60).

Alternatively, or in addition, in steps (d) or (e), the step of temporarily confirming the ability to deliver the pacing therapy using the elongated stylet may further include a step of verifying a pacing capture of the cardiac tissue or the presence of a predetermined feature on the cardiac electrogram, as known in the art of cardiac pacing. Recording of certain electrogram characteristics may be considered indicative of the first distal end electrode being in the vicinity of the left bundle branch, such as a recording of a discrete left bundle branch potential, typically 25-35 ms in front of the QRS, or a discrete sharp signal indicative of Purkinje potential recorded less than 25 ms in front of the QRS.

Furthermore, if the distal end of the elongated stylet includes a first electrode and a second electrode, the step of temporarily confirming the ability to deliver the pacing therapy in steps (d) or (e) may include a step of temporary pacing or monitoring an electrogram using one of the first electrode or the second electrode in a unipolar fashion or both the first electrode and the second electrode in a bipolar fashion.

If the intended cardiac pacing therapy is to pace the left bundle branch area, the step of temporarily confirming the ability to deliver the pacing therapy in steps (d) or (e) may further include a step of temporary pacing the left bundle branch area using the distal end of the elongated stylet to verify the ability to capture thereof.

Figures 9A, 9B:
FIGS. 9a through 9f show various consecutive stages of deployment of the cardiac pacing lead using the delivery system and the method of the present invention.

FIG. 9a shows the first position of the sheath 18 adjacent to the cardiac tissue. The first step may be the deployment of the elongated stylet 20 to touch the cardiac tissue, as seen in FIG. 9b. An ECG or another electrogram may be recorded (or temporary pacing may be performed) using the first electrode of the distal end of the elongated stylet 20.

Figures 9C, 9D:
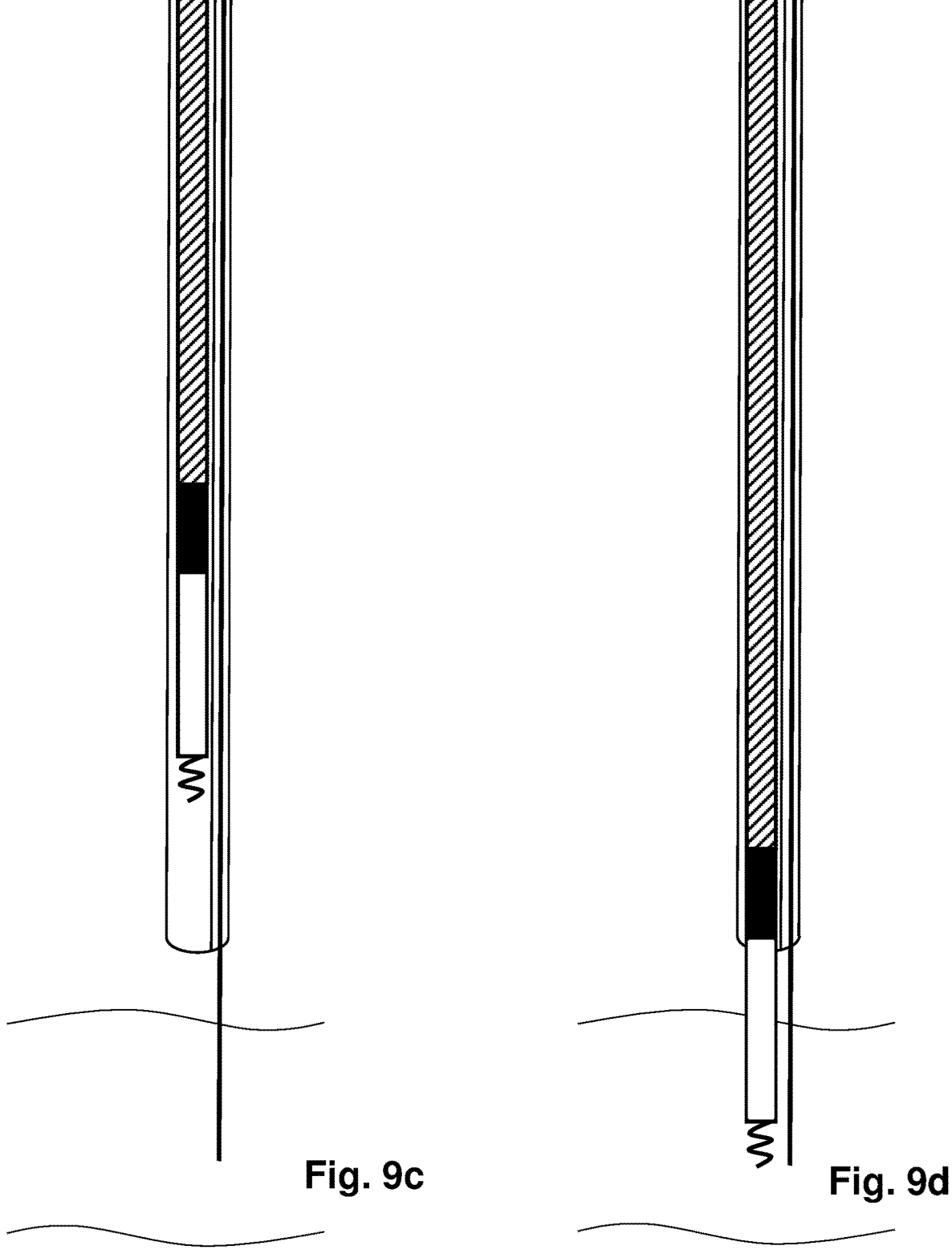

The elongated stylet 20 may then be gradually inserted into the cardiac tissue using the metered advancement mechanism on the retaining hub 16 of the delivery sheath 18, as seen in FIG. 9c. The first electrode 22 at the distal end 20 may be continuously or intermittently monitored to detect the depth of the insertion—for example by using impedance measurements, as described in our previous patent applications. The first electrode 22 may be used to record paced ECG, recording of conduction system potentials, and other suitable metrics as may be customary, in addition to monitoring the position of the proximal portion of the elongated stylet 20 in relationship to the retaining hub 16 and observing the stylet tip on fluoroscopy or other imaging methods. In that sense, the elongated stylet 20 may be used in a manner similar to that of a pacing wire. Once the desired depth is reached, a temporary pacing therapy delivery may be verified using the distal end 22. If the desired pacing performance is not achieved, the elongated stylet 20 may be advanced further to a different depth in the cardiac tissue. If none of the depths are shown to be sufficient for delivery of the intended therapy, the elongated stylet 20 may be retracted, and the delivery system 10 may be moved to another nearby location to try again. Importantly, at this point in the procedure, the only trauma to the heart tissue is the penetration of a thin stylet tip and not the larger helical tip 31 of the cardiac pacing lead 30. The procedure of FIGS. 9a through 9c may be repeated one or more times until the proper implantation position and a suitable implantation depth are found. Although the trauma to the heart tissue is minimal, it is suggested that redeployment of the delivery system 10 is not done more than a few times in order to further limit tissue damage.

As can be understood from above, a key advantage of the system of the invention is the ability to pre-check the exact location and depth of the pacing lead implantation to ensure that adequate performance is demonstrated-all before the actual pacing lead 30 is even inserted into the cardiac tissue. In case no adequate pacing performance can be attained, a decision to switch to an alternative pacing treatment may be made, for example, a bi-ventricular pacing. The delivery system may be withdrawn, and further tissue damage may be avoided.

In further embodiments, steps 9a through 9c may be conducted before the pacing lead 30 is even loaded into the delivery sheath 18. In case no adequate pacing performance can be attained, there will be no expense of opening and discarding the cardiac pacing lead 30 in this case.

Once the cardiac pacing performance is verified in step 9c, the pacing lead 30 may be deployed while the elongated stylet 20 is still in place to maintain the position of the delivery sheath 18, see FIG. 9d. Fluoroscopic or other imaging may be used to confirm the position of the cardiac lead helical tip 31 to be next to the distal electrode 22 at the end of the elongated stylet 20. Cardiac pacing may also be conducted using the electrodes of the pacing lead 30 to confirm adequate pacing and monitoring function.

Figures 9E, 9F:
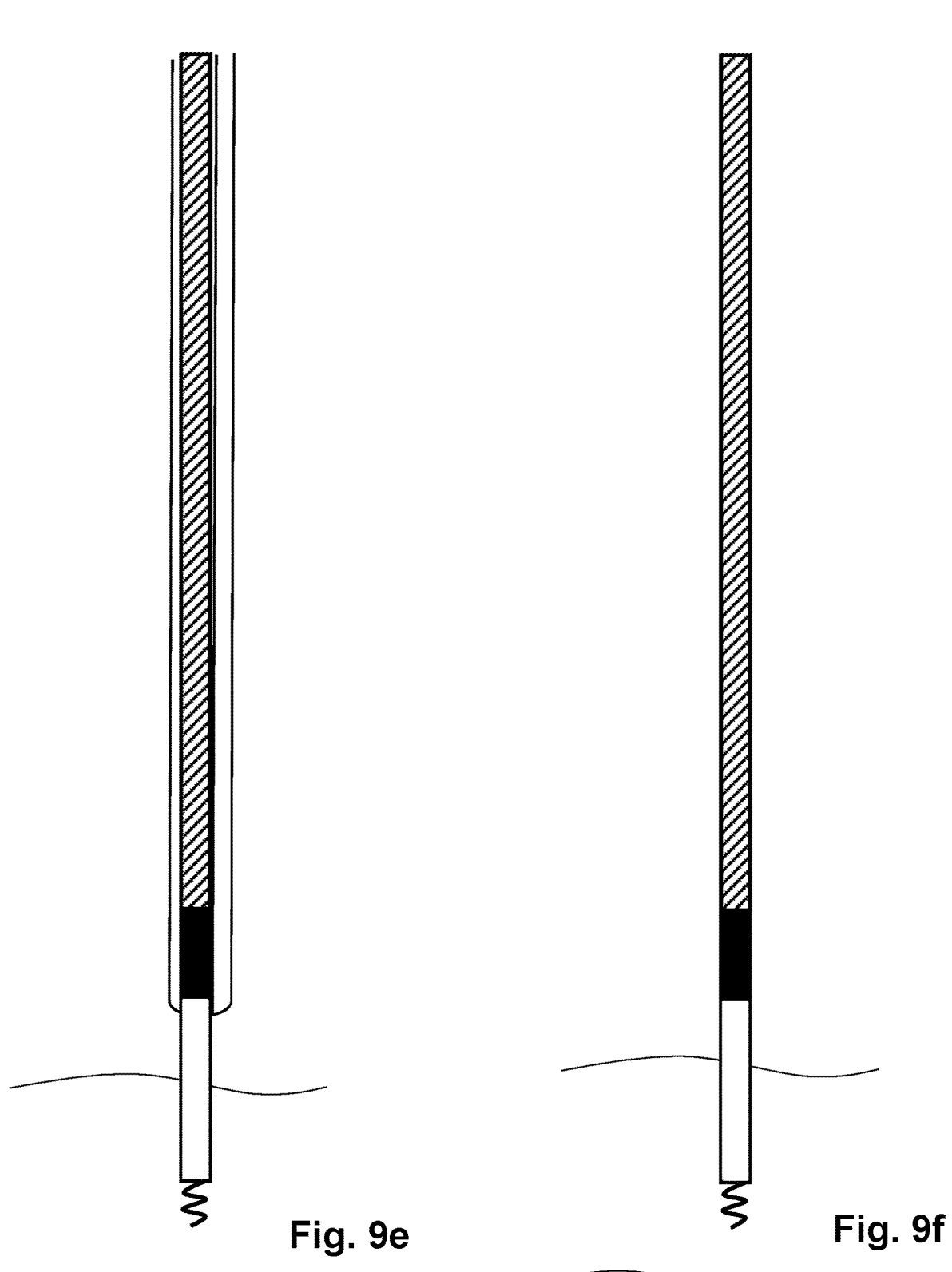

Once the pacing performance using the pacing lead 30 is confirmed, the elongated stylet 20 may be withdrawn, see FIG. 9*e*. The delivery sheath 18 is then also withdrawn, as seen in FIG. 9*f*, and the lead implantation procedure is finished as described above.

In addition to the less traumatic implantation advantage (by avoiding the damage from multiple lead deployments), the present invention allows expediting the implantation procedure by rapidly assessing the adequacy of the selected implantation site, thereby reducing the overall procedure time, especially in more challenging patients.

Improvement of Orthogonality of Lead Implantation

In addition to the steps described above, the present invention may allow for an optional maneuver described below aimed at improving the quality of lead implantation, namely at achieving implantation at about a 90-degree angle to the target cardiac tissue. The approach to the interventricular septum, for example, may not necessarily be at an optimal 90-degree angle. Various curved shapes of the distal end of the delivery sheath are typically used to make the approach more orthogonal, but this approach is still not able to accomplish the desired orientation of the pacing lead and cardiac tissue. The present invention may also be advantageously used to further improve the pacing lead deployment and achieve an optimal orthogonal orientation of the distal end of the lead during deployment.

Figure 10A:
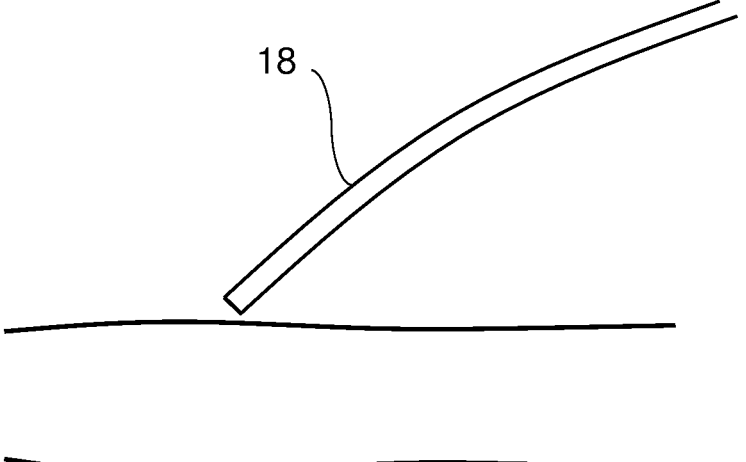
FIGS. 10a through 10k show various stages of deployment of the cardiac pacing lead with improved orthogonality.
Figure 10B:
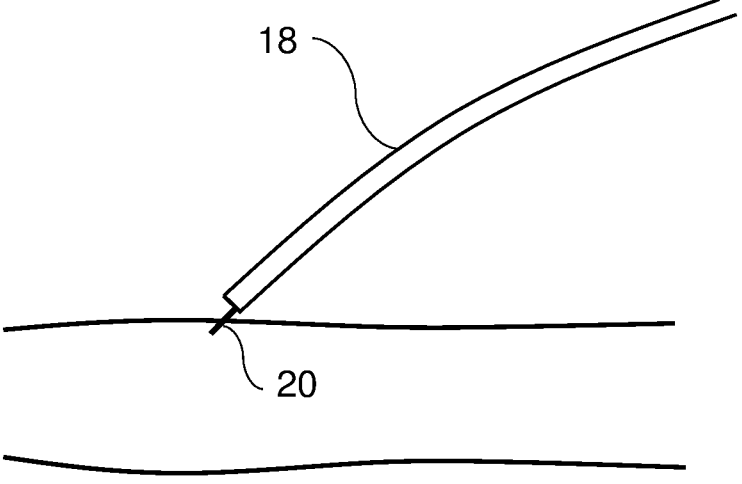
Figure 10C:
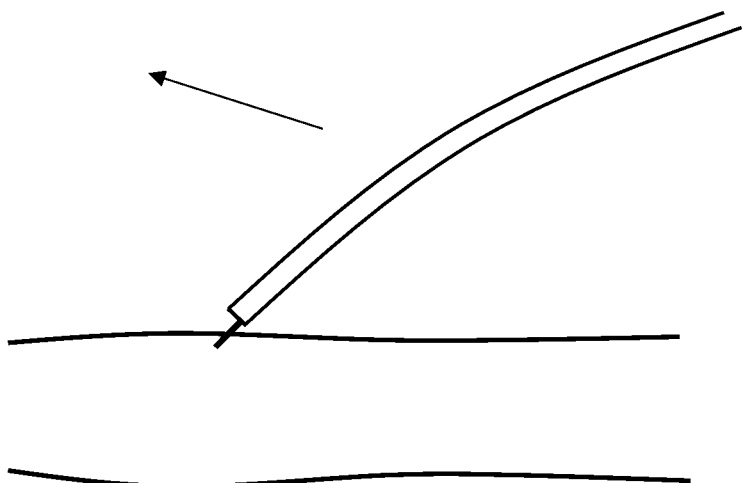
Figure 10D:
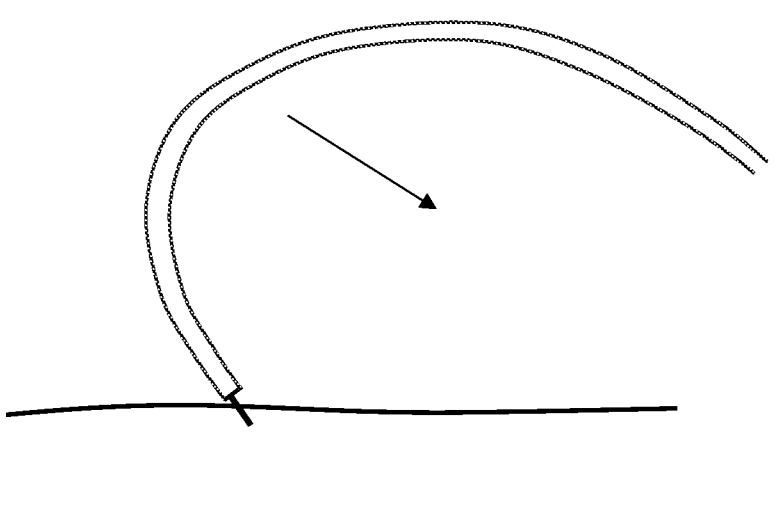
Figure 10E:
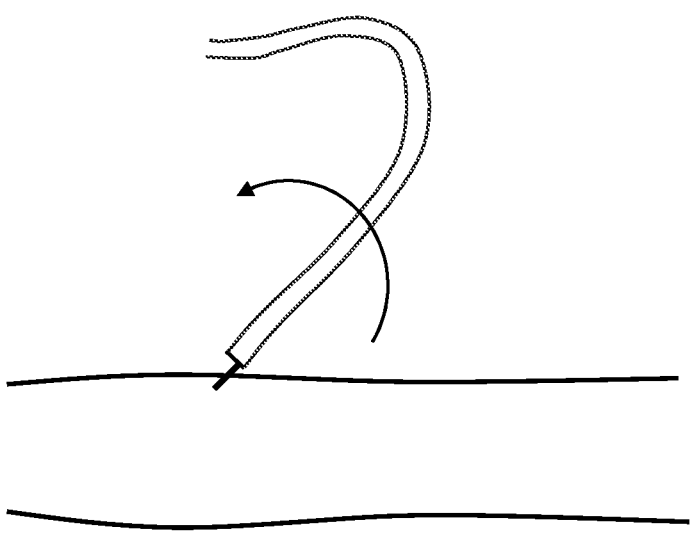

FIGS. 10*a* through 10*k* illustrate the method of implantation according to the invention. The initial approach of the distal end of the delivery sheath 18 containing the cardiac pacing lead 30 and the elongated stylet 20 may be either at: (i) an acute angle to the septum, as shown in FIG. 10*c*, (ii) at an obtuse angle to the septum, as seen in FIG. 10*d*, or (iii) the plane of the delivery sheath curve may itself be at an acute or an obtuse angle to the septum, as seen in FIG. 10*e*.

The present invention may be used to facilitate optimal pacing lead delivery in the following way. Once the tip of the delivery sheath 18 is positioned next to the cardiac tissue at the first or at additional positions targeted for implantation (as seen in FIG. 10*a*), the distal end of the elongated stylet 20 may be advanced to provisionally engage with the underlying tissue at a "shallow" depth, typically 1-3 mm or so (as seen in FIG. 10*b*). The distal end of the sheath 18 is now "hooked" onto the cardiac tissue. After the initial provisional shallow engagement with the tissue, the distal end of the elongated stylet 20 now acts as an anchor and allows the operator to manipulate the delivery sheath to achieve a proper angle of implantation for the remaining steps of the procedure.

If the initial angle between the distal end of the delivery sheath 18 and the underlying tissue was acute, as seen in FIG. 10*c*, the operator may push on the delivery sheath and advance it forward. This causes a bowing effect of the delivery sheath 18 to arch into a desired position shown in FIG. 10*f*.

Figure 10F:
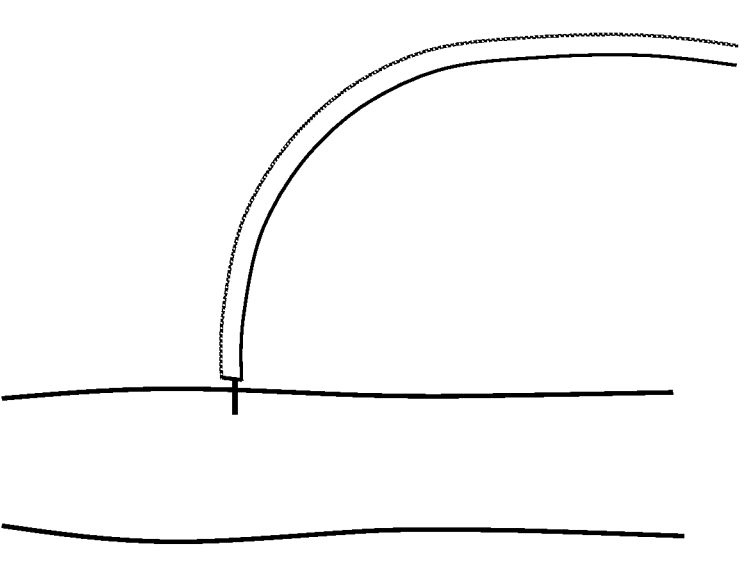
Figure 10G:
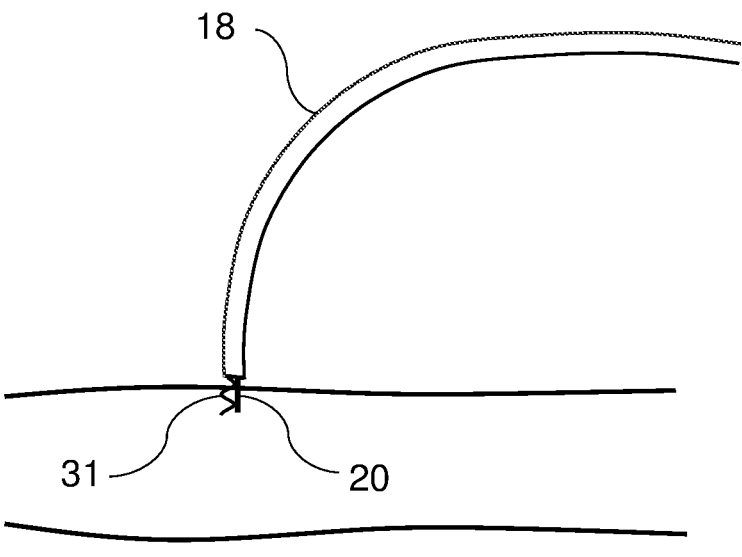

If the initial angle between the distal end of the delivery sheath 18 and the underlying tissue was obtuse, as seen in FIG. 10*d*, the operator may pull back on the delivery sheath 18 to achieve the same proper angle as seen in FIG. 10*f*.

If the plane of the delivery sheath curve was tilted to the surface of the cardiac tissue as seen in FIG. 10*e*, the operator may apply torque in the appropriate direction to rotate the plane to be perpendicular to the cardiac tissue, as seen again in FIG. 10*f*.

As can be understood by a person skilled in the art, a combination of pull and torque or push and torque may be required in order to take advantage of the distal tip of the elongated stylet 20 acting as an anchor in the cardiac tissue.

Once the orientation of the delivery sheath 18 is satisfactory, the operator may also engage the helical tip 31 of the lead 30 to a shallow depth in the cardiac tissue on a provisional basis. This is an optional step and it may or may not be required for further delivery steps depending on specific circumstances-see FIG. 10*g*.

Figure 10H:
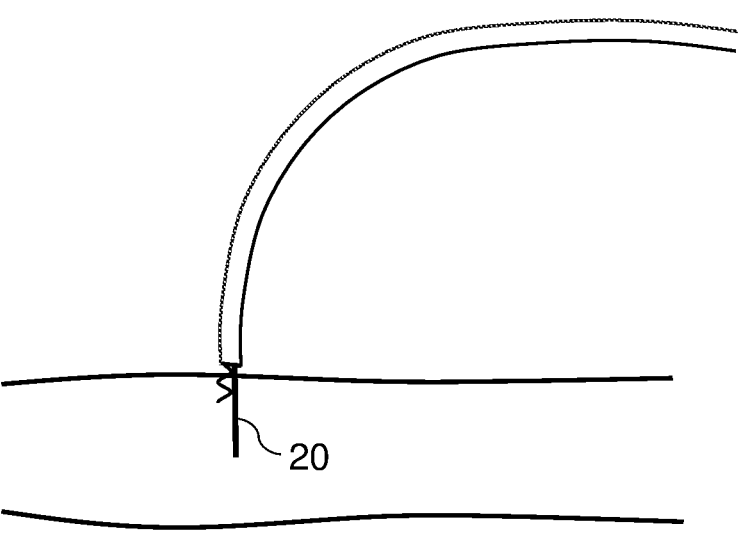
Figure 10I:
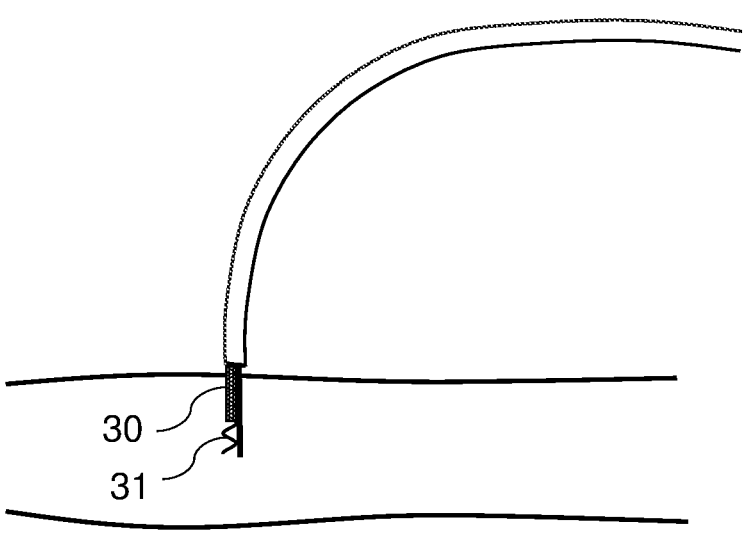

The distal end of the elongated stylet 20 may then be further advanced into the cardiac tissue-see FIG. 10*h*—to precheck the implantation position as described above in greater detail. Once the implantation position is confirmed, the pacing lead 30 may be advanced to match the position of the helical tip 31 with the position of the distal end of the elongated stylet 20 (see FIG. 10*i*)—as verified, for example, using imaging techniques, or as confirmed by a satisfactory temporary pacing using the pacing lead itself.

Figure 10J:
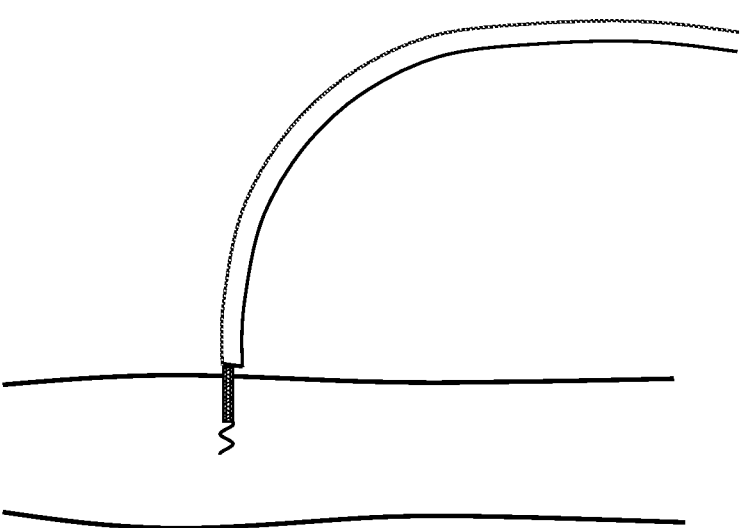
Figure 10K:
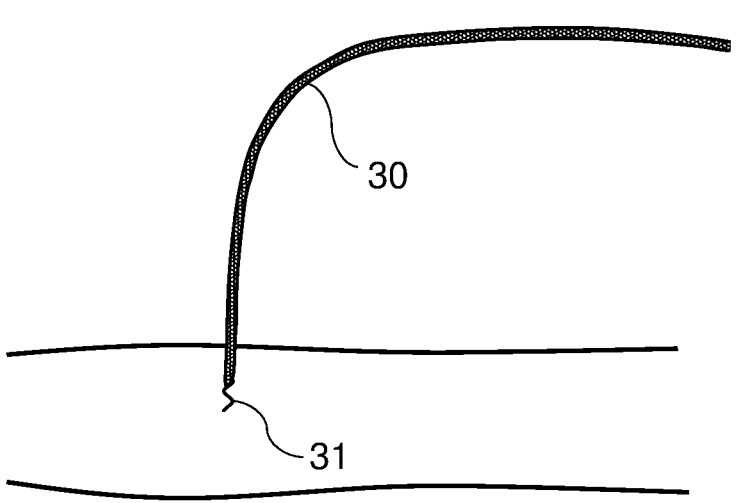

The elongated stylet 20 may then be withdrawn (as seen in FIG. 10*j*), which is followed by withdrawal of the delivery sheath 18—leaving the cardiac pacing lead 30 with the helical tip 31 implanted orthogonally to the cardiac tissue.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A delivery system for implantation of a cardiac pacing lead comprising an elongated delivery sheath sized to accept the cardiac pacing lead inside thereof, the elongated delivery sheath further containing an elongated stylet positioned along the cardiac pacing lead, the elongated stylet having a distal end and a proximal end, the distal end of the elongated stylet comprising a first distal electrode configured to provide a first electrical connection to a first electrode attachment at the proximal end of the elongated stylet for temporary cardiac pacing or electrogram monitoring to pre-check an implantation position prior to deployment of the cardiac pacing lead, the first electrode attachment configured to be electrically connected to an external cardiac stimulator and monitor, wherein the cardiac pacing lead and the elongated stylet may be advanced inside the delivery sheath independent of one another.

2. The delivery system, as in claim 1, wherein the cardiac pacing lead comprises a lead body and a distal lead electrode configured to remain inside a target cardiac tissue upon deployment therein.

3. The delivery system, as in claim 1, wherein the elongated stylet further comprises a first electrode attachment at the proximal end thereof configured to be electrically connected to the first distal electrode of the elongated stylet.

4. The delivery system, as in claim 1, wherein the distal end of the elongated stylet comprises a second electrode configured to be in electrical connection with the second electrode attachment at the proximal end of the elongated stylet.

5. The delivery system, as in claim 1, wherein the delivery sheath comprises a retaining hub at a proximal end thereof, the retaining hub is configured to releasably retain the elongated stylet and to allow a controlled advancement of the elongated stylet in a known relationship between the position of the distal end of the elongated stylet and a distal end of the delivery sheath or a distal end of the cardiac pacing lead retained therein.

6. The delivery system, as in claim 5, wherein the retaining hub comprises a stylet channel configured to retain and facilitate advancement of the elongated stylet through the delivery sheath.

7. The delivery system, as in claim 6, wherein the stylet channel of the retaining hub comprises a threaded channel configured to accept a corresponding threaded handle at the proximal end of the elongated stylet, so as to facilitate a metered advancement of the elongated stylet inside the delivery sheath by rotating the threaded handle cooperating with the threaded channel of the retaining hub.

8. The delivery system, as in claim 7, wherein either the threaded handle of the elongated stylet or the threaded channel of the retaining hub contains a position-indicating indicia configured to monitor advancing or withdrawing the elongated stylet within the elongated delivery sheath.

9. The delivery system, as in claim 5, wherein the retaining hub is configured to removably attach to the proximal end of the delivery sheath.

10. The delivery system, as in claim 5, wherein the retaining hub is incorporated with the proximal end of the delivery sheath.

11. The delivery system, as in claim 1, wherein the delivery sheath contains the cardiac pacing lead and the elongated stylet in the same lumen and side-by-side.

12. The delivery system, as in claim 1, wherein the delivery sheath comprises a first lead lumen and a second stylet lumen configured to slidably retain the respective cardiac pacing lead and the elongated stylet within thereof.

13. A delivery system for implantation of a cardiac pacing lead comprising an elongated delivery sheath having a first lead lumen with the cardiac pacing lead slidably positioned inside thereof, the elongated delivery sheath further comprising a second stylet lumen along the first lead lumen, the second stylet lumen is occupied by an elongated stylet slidably positioned inside thereof, the elongated stylet having a distal end and a proximal end, the distal end of the elongated stylet comprising a first distal electrode configured to provide a first electrical connection to the proximal end of the elongated stylet, wherein the cardiac pacing lead and the elongated stylet may be advanced inside the respective first lead lumen and the second stylet lumen of the delivery sheath independent of one another.

14. A method for delivery of a cardiac pacing lead selected to provide a pacing therapy to a target cardiac tissue comprising the steps of:

a. providing a delivery system comprising an elongated delivery sheath containing the cardiac pacing lead and an elongated stylet having a first distal electrode inside thereof, b. positioning a distal end of the delivery sheath adjacent to a target cardiac tissue, c. advancing the elongated stylet to a first position for implantation of the cardiac pacing lead such that the first distal electrode of the elongated stylet is positioned within the target cardiac tissue, d. pre-check the first position in the cardiac tissue by temporarily confirming the ability to deliver the pacing therapy thereat using the first distal electrode of the elongated stylet to perform at least one of temporary pacing or electrogram monitoring, e. if the confirmation is not reached in step (d), changing the depth of the distal end of the elongated stylet or repositioning the delivery system and the elongated stylet to a second position or further positions and repeating the step of temporarily confirming the ability to deliver the pacing therapy thereat, f. upon reaching the confirmation in step (d) or step (e), deploying the cardiac pacing lead to the position next to the distal end of the elongated stylet, and g. withdrawing the elongated stylet and removing the delivery system while leaving the cardiac pacing lead in the target cardiac tissue.

15. The method for delivery of the cardiac pacing lead, as in claim 14, wherein in steps (d) or (e), the step of temporarily confirming the ability to deliver the pacing therapy using the elongated stylet further comprises a step of pacing using the distal end thereof or a step of monitoring an electrogram signal acquired using the distal end of the elongated stylet.

16. The method for delivery of the cardiac pacing lead, as in claim 14, wherein in steps (d) or (e) the step of temporarily confirming the ability to deliver the pacing therapy using the elongated stylet comprises a step of confirming a pacing capture of the cardiac tissue or a presence of a predetermined feature on the cardiac electrogram.

17. The method for delivery of the cardiac pacing lead, as in claim 14, wherein in step (a), the distal end of the elongated stylet comprises at least a first electrode and a second electrode, and wherein in steps (d) or (e) the step of temporarily confirming the ability to deliver the pacing therapy further comprises a step of temporary pacing or monitoring an electrogram using one of the first electrode or the second electrode in a unipolar fashion or both the first electrode and the second electrode in a bipolar fashion.

18. The method for delivery of the cardiac pacing lead, as in claim 14, wherein the pacing therapy is selected to pace a left bundle branch area, and wherein in step (d) or (e) the step of temporarily confirming the ability to deliver the pacing therapy further comprises a step of temporary pacing the left bundle branch area using the distal end of the elongated stylet to verify the ability to capture thereof.

* * * * *